United States Patent [19]
Goforth

[11] Patent Number: 5,817,066
[45] Date of Patent: Oct. 6, 1998

[54] BULB-TYPE IRRIGATION SYRINGE

[76] Inventor: Thomas Leonard Goforth, 1851 Chapel Hill Church Loop, Marion, N.C. 28752

[21] Appl. No.: 728,170

[22] Filed: Oct. 9, 1996

[51] Int. Cl.⁶ ................................................. A61M 5/178
[52] U.S. Cl. .......................... 604/212; 604/217; 604/275; 215/237
[58] Field of Search ..................... 220/337, 338; 215/3, 235, 237; 222/209; 99/345; 604/48, 73, 75, 77, 78, 181, 187, 257, 217, 275, 212

[56] References Cited

U.S. PATENT DOCUMENTS

| | | | |
|---|---|---|---|
| 3,215,142 | 11/1965 | Buono | 604/217 |
| 4,693,709 | 9/1987 | George et al. | 604/212 |
| 4,713,219 | 12/1987 | Gerken et al. | 422/102 |
| 5,254,314 | 10/1993 | Yu et al. | 422/102 |
| 5,270,011 | 12/1993 | Altherr | 422/102 |

Primary Examiner—Wynn Wood Coggins
Assistant Examiner—Deborah Blyveis
Attorney, Agent, or Firm—John P. Halvonik

[57] ABSTRACT

The invention is an improved bulb-type irrigation syringe having an open end that is of a funnel shaped construction and having a recloseable lid that fits onto the top of the funnel shaped end of the syringe and down inside the top barrel portion of the syringe. The top of the syringe is modified by making it larger so as to resemble a funnel shaped construction. The lid is able to frictionally fit inside the barrel of the syringe creating an airtight frictional seal and has another aperture in order to hold a squeeze bulb in airtight frictional connection as well. A squeeze bulb is normally attached to the top of the syringe and in this invention may be closed inside the barrel of the syringe by simply closing the lid on top of the funnel shaped syringe. The pivoting lid has an aperture that is adapted to hold the neck of the squeeze bulb in airtight frictional connection with the lid when the lid is closed both the lid and the squeeze bulb will be in airtight frictional connection with the barrel of the syringe.

2 Claims, 7 Drawing Sheets

FIG. 7

BULB-TYPE IRRIGATION SYRINGE

TECHNICAL FIELD

This invention relates to syringes and more particularly to syringes of the type which may be used for feeding purposes.

1. Background to the Invention

The invention relates to the field of irrigation syringes used for feeding and in particular to a feeding syringe having a recloseable lid with an opening that is adapted to secure a squeeze bulb in the opening.

2. Description of The Prior Art

Medical irrigation syringes, for example, are often employed for irrigating wounds during surgery, flushing and draining body cavities but are also used for administering medication and feedings to patients. Irrigation syringes are used for many other medical purposes than that mentioned above but this invention is primarily concerned with such devices which are used for feeding purposes. The basic function of bulb-type syringes is as follows. Syringes of the type having separately formed bulb and barrel members usually include a bulb having a compressible bulbous portion connected to a generally cylindrical connector end portion which end portion is connected with the barrel by a tight frictional fit but is usually made to be manually separable from the barrel so that the barrel can be used alone as a funnel. The syringe may be operated to produce a positive or negative pressure in the bore. With the cap removed from the tip of the syringe, the bulb may be, for example, compressed by placing two fingers under the annular or preferably under tabs, and pressing the thumb in center of the proximal wall distally compressing or collapsing the bulb to effect, for example, the discharge of air from the bore and the bulb, the air flowing out the tip. While holding the bulb compressed, the syringe tip may be inserted into a fluid such as a liquid solution and the pressure of the thumb on the bulb released so that the resiliency of the bulb returns the bulb to it's uncompressed or normal bulbous shape creating a negative pressure within the bore so that liquid is drawn into the bore and bulb. There have been several problems associated with bulb-type syringes when used for feeding purposes. Patients who will not readily accept nourishment, liquids or medications orally many times require the use of such syringes. The tip of the syringe is placed inside the mouth of the patient and the contents are slowly and gently forced inward for consumption. (1) A problem that many healthcare providers encounter during this procedure is getting the contents of the meal which may be pureed (ground or blended up so as not to require chewing before swallowing) such as meats, fruits and vegetables down into the barrel of the syringe. This can be a difficult and time consuming process since the user must remove the bulb from the syringe and use a spoon to shovel the feeding into the mouth of the barrel of the syringe who's diameter is smaller than that of the spoon. Not only can a mess be made in this procedure but some of the food intended for the patient's consumption may be lost as the user attempts to pack and channel the food into the barrel. (2) Another problem that healthcare providers encounter in the use of these syringes is in the feeding of patients requiring the use of a feeding tube. A feeding tube is either inserted through the nasal cavities (Nasogastric) and down into the stomach or surgically implanted through the abdomen of the patient and anchored into the stomach (Gastric feeding tube). Both methods require the use of a syringe to administer medication or supplemental liquid feedings to the patient. The tip at the distal end of the syringe is connected into the patient's feeding tube. The bulb is removed and the syringe is then employed as a funnel which channels liquid nourishment or medication into the feeding tube. These supplemental feedings come in cans or bottles and must be carefully poured into the barrel of the syringe as not to make a mess. The opening in which to pour the solution is rather small as fluids do not always pour smoothly from a can or bottle. Also the user may have to pour the liquids into a moving barrel because the syringe is connected to the feeding tube which is directly attached to either the patient's face or abdomen and if the patient throws their head or twist their body the feeding tube goes with them along with the connected syringe. (3) Another problem encountered by healthcare providers is the sheer number of times the user must extract and engage the bulb to and from the barrel of the syringe in the course of feeding a single patient. The bulb must be fitted into frictional connection with the barrel of the syringe which is acheived by the syringe being made of rigid plastic and the bulb being made of a rubbery material. Together they form an airtight frictional seal but unfortunately the two materials do not always create a perfect airtight seal everytime the user attempts to connect the two together and may end up having to repeat the process several times until a seal is achieved. The user in the course of feeding a single patient may have to seperate and re-attach the bulb to the syringe many times.(4) Another problem encountered by healthcare providers in using a bulb-type syringe for feeding is having to keep up with the bulb once it is extracted from the syringe because it is very difficult for the user to hold the syringe and the extracted bulb in one hand and administer medication or feeding with the other hand. (5) Another problem encountered in the use of a bulb-type syringe for feeding is the risk of the user contaminating the neck of the bulb with their fingers during manipulation of the bulb to and from the barrel of the syringe. If the neck or mouth of the bulb were contaminated through contact with the user's hand during manipulation the patient could be indirectly exposed to whatever was on the user's hand. This procedure is not a sterile process but for the sake of the patient it should remain clean at all times as to minimize the exposure of germs and pathogens from coming into contact with the patient. (6) Another problem encountered by healthcare providers is while the patient is being fed by means of a feeding tube the user may encounter what is called Reflux (a backward flow of duodenal contents from the stomach) that force any fluid in the feeding tube or connected syringe to quickly flow in a backward motion and if the user does not kink off the feeding tube or quickly reinsert the bulb back into the syringe the contents will overflow. (7) Another problem encountered by healthcare providers in the use of a bulb-type syringe is in the compression of the bulb. The user compresses the bulb with their thumb and use their index and middle fingers which are clasped over finger tabs for leverage. It is possible to compress the bulb without the aid of these finger tabs but it is more difficult and time consuming. In the process of re-attaching the bulb to the syringe the user may move the syringe around in order to frictionally connect the bulb. Once the bulb is connected to the syringe the user may need to manipulate the syringe once again in order to line up the finger tabs for clasping.

SUMMARY OF THE INVENTION

The invention is an improved bulb-type irrigation syringe having an open end that is of a funnel shaped construction and having a recloseable lid that fits onto the top of the funnel shaped end of the syringe and down inside the top barrel portion of the syringe. The top of the syringe is modified by making it larger so as to resemble a funnel shaped construction. The lid is able to frictionally fit inside the barrel of the syringe creating an airtight frictional seal and has another aperture in order to hold a squeeze bulb in airtight frictional connection as well. A squeeze bulb is normally attached to the top of the syringe and in this invention may be closed inside the barrel of the syringe by simply closing the lid on top of the funnel shaped syringe. The pivoting lid has an aperture that is adapted to hold the neck of the squeeze bulb in airtight frictional connection with the lid. When the lid is closed both the lid and the squeeze bulb will be in airtight frictional connection with the barrel of the syringe. It is an object of the invention to provide a bulb-type feeding syringe system that the user does not have to hold the squeeze bulb in hand or otherwise manipulate the squeeze bulb other than during the actual squeezing process. This would eliminate the need of the user having to keep up with the bulb once it is extracted from the syringe and minimize the chance of the user's fingers contaminating the neck of the bulb since the user can manipulate the bulb without actually touching it.

Another object of the invention is to provide an easier to use bulb-type feeding syringe system where the squeeze bulb can be extracted or inserted to and from the barrel of the syringe via a snap on pop-top bulb extracting lid and eliminate the need for hand manipulation of the squeeze bulb.

Another object of the invention is to provide an easier to use bulb-type feeding syringe system having a larger surface area at the top of the funnel of the syringe whereby the user may pour liquids or place foods into the syringe quicker and more efficenty without making a mess or wasting the feeding in the process. Another object of the invention is to provide an easier to use bulb-type feeding syringe system that can prevent spillage due to regurgitation and other actions by virtue of a large feeding funnel at the top of the feeding syringe that is in conjunction with a snap on lid over the top of the funnel portion of the syringe. Another object of the invention is to provide a easier to use bulb-type feeding syringe system that can be held in the user's fingers without having to resort to the manufacture of finger tabs of the feeding syringe. Other objectives of the invention will become apparent to those skilled in the art once the invention has been shown and described.

DESCRIPTIONS OF THE DRAWINGS

FIG. 5 (A&b)are perspective views as to the pivoting function in accordance with the present invention.

DESCRIPTION OF THE PREFERRED EMBOIDIMENT

Figure 1:
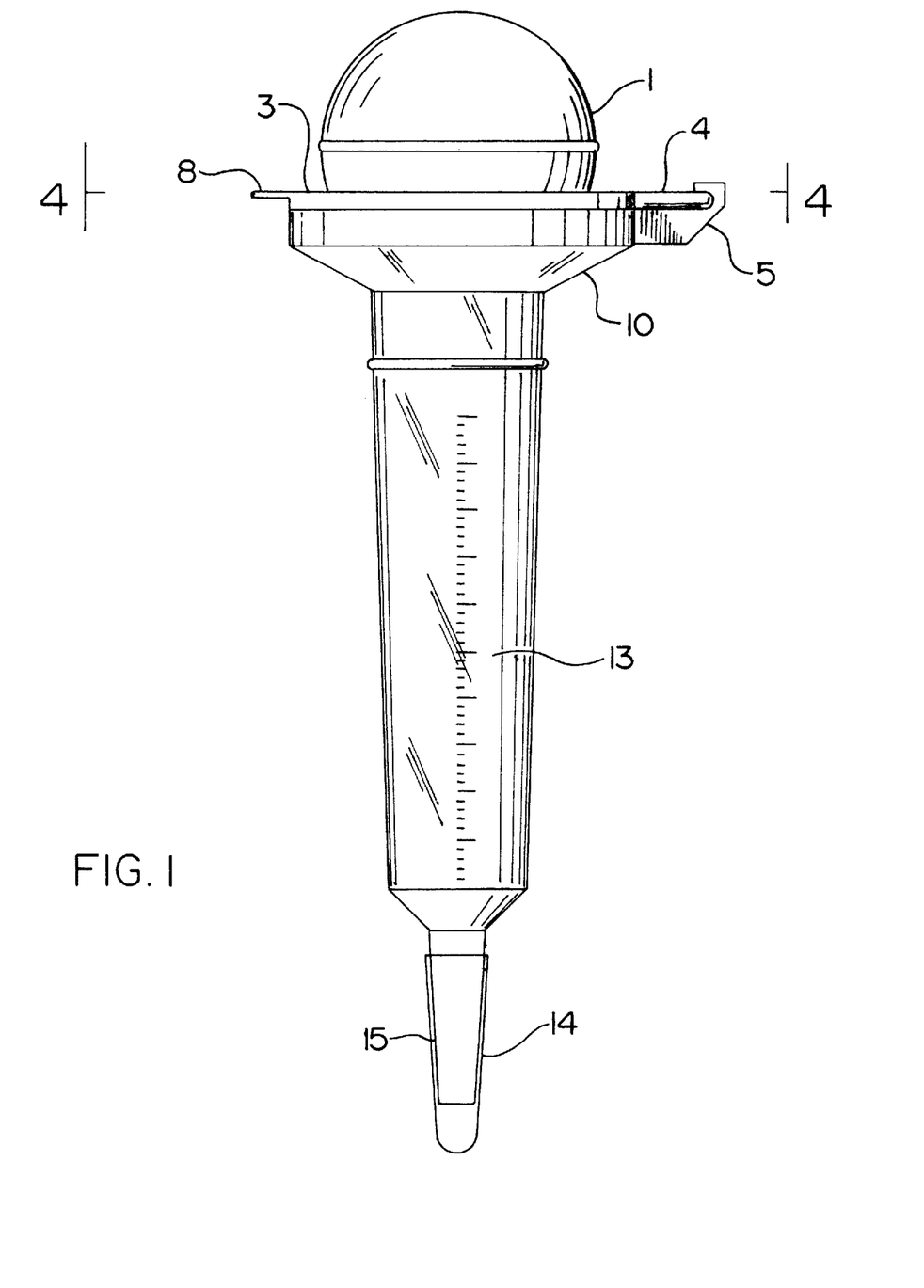
FIG. 1 is a side elevational view of a syringe in accordance with the present invention.
Figure 2:
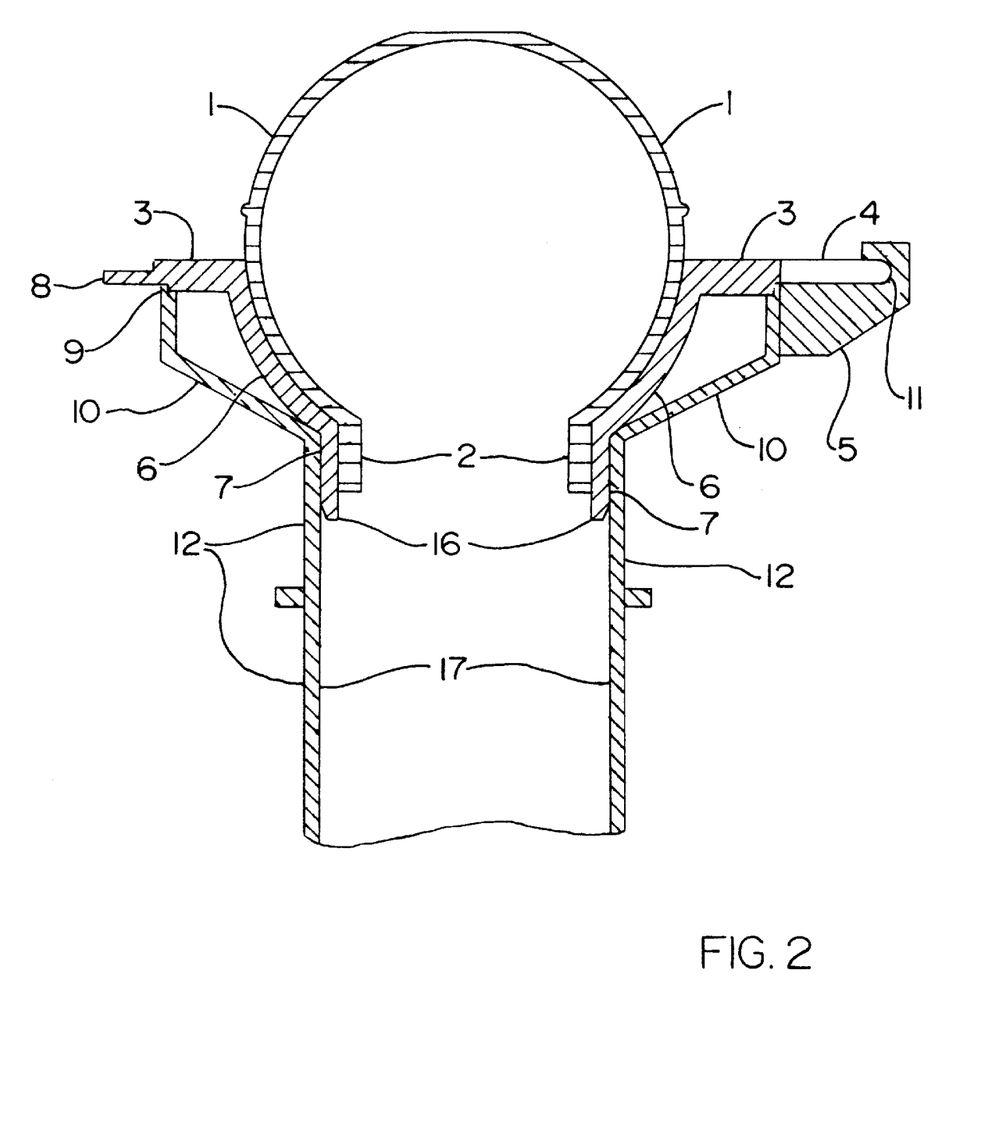
FIG. 2 is an enlarged, fragmentary, longitudinal, crossectional view of the syringe of FIG. 1
Figure 3:
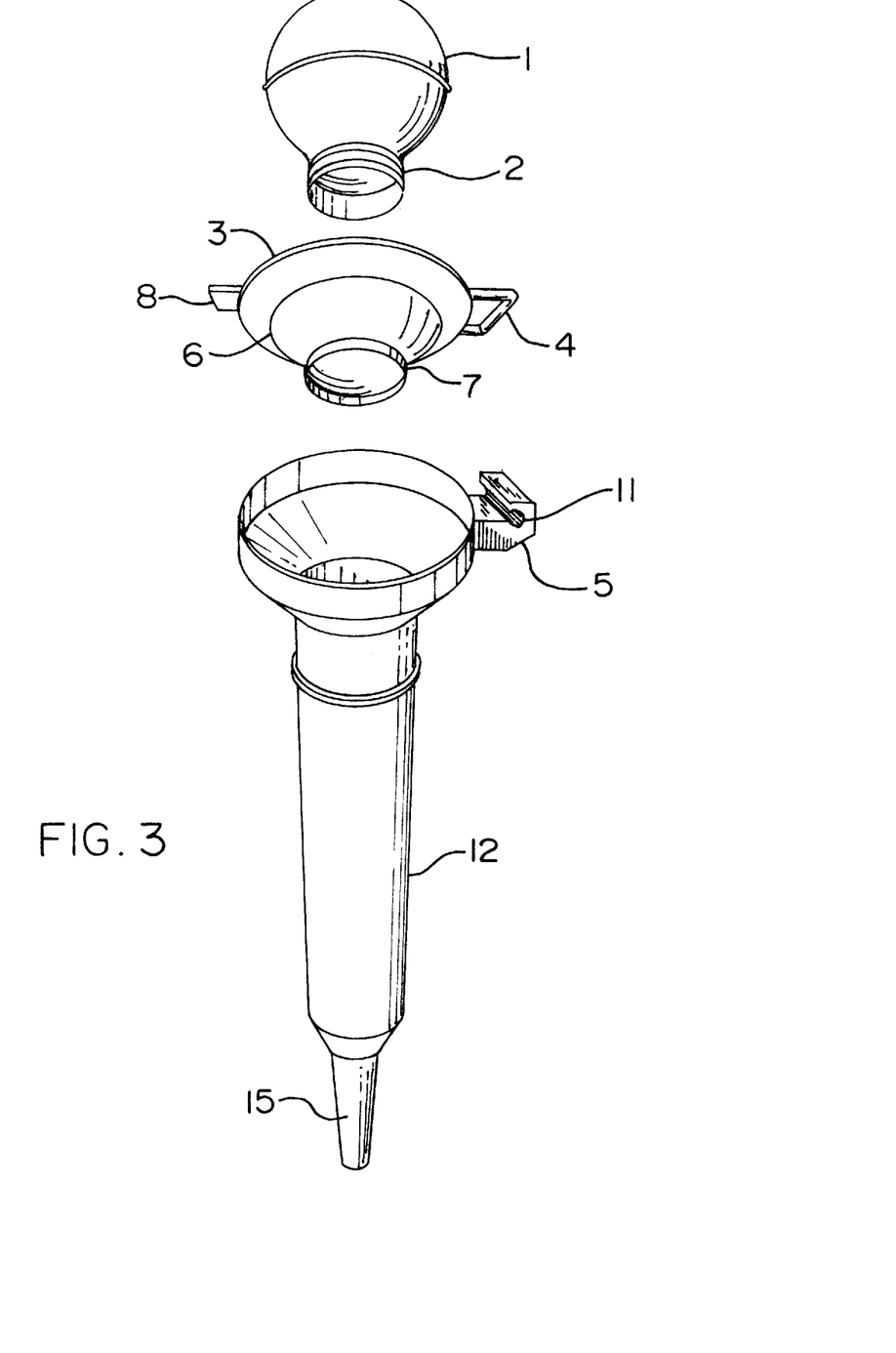
FIG. 3 is an exploded perspective view and parts in accordance with the present invention.
Figure 4:
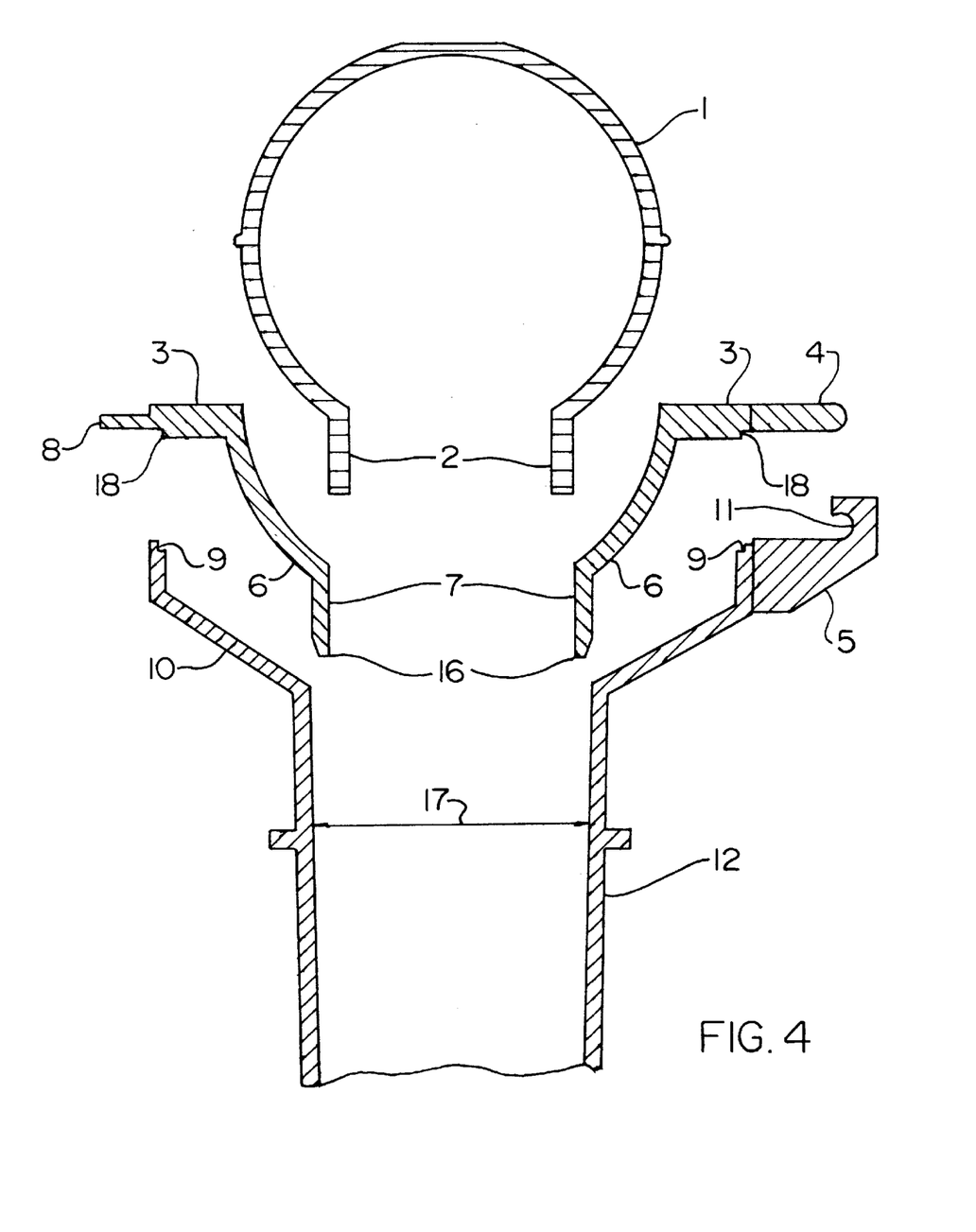
FIG. 4 is an enlarged, fragmentary, longitudinal, crossectional view of FIG. 3
Figure 5A:
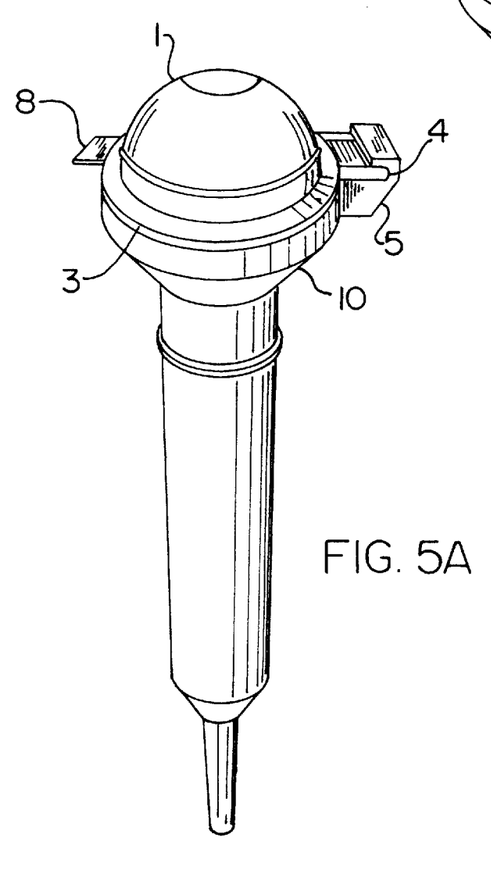
Figure 5B:
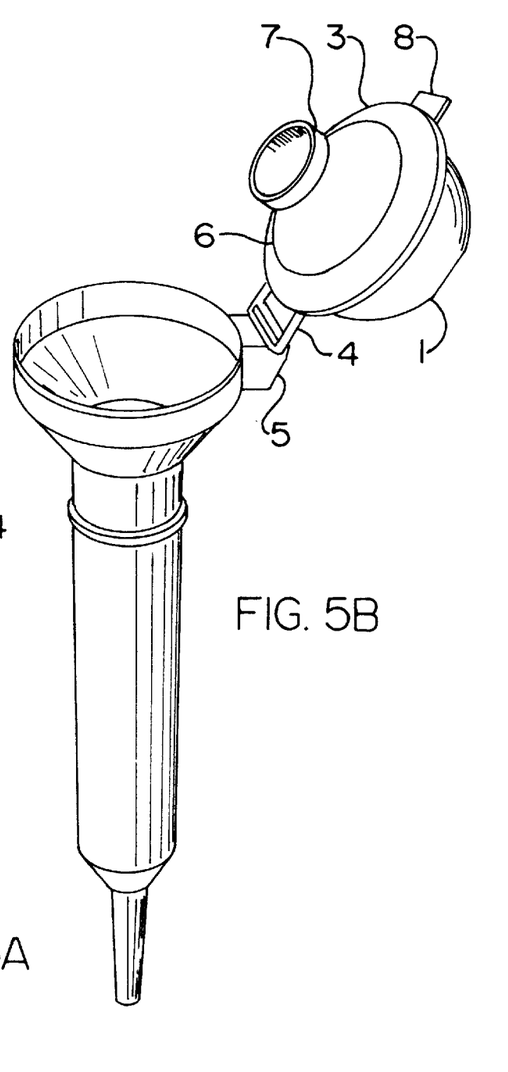
Figure 6:
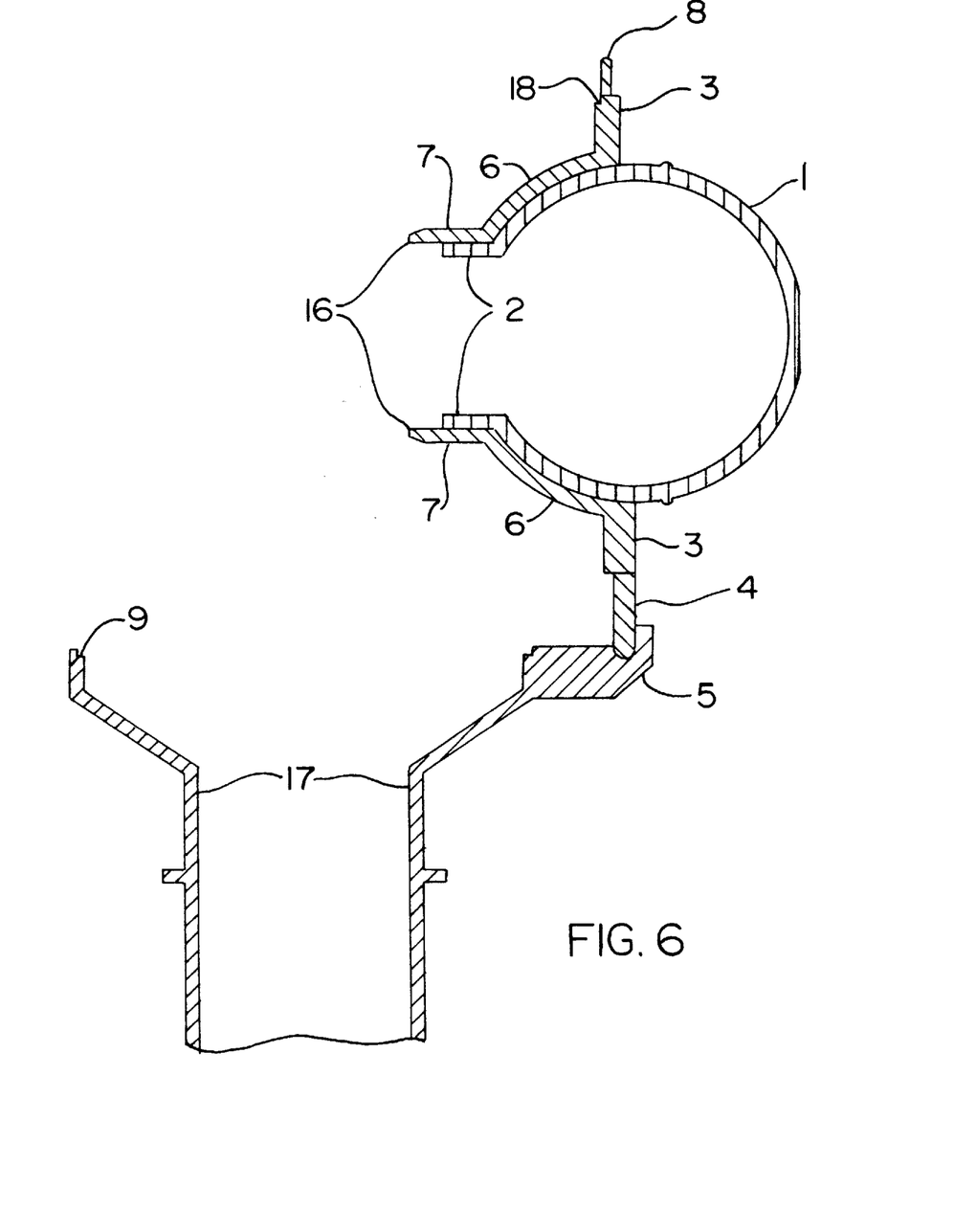
FIG. 6 is an enlarged, fagmentary, longitudinal, crossectional view of FIG. 5. (B)
Figure 7:
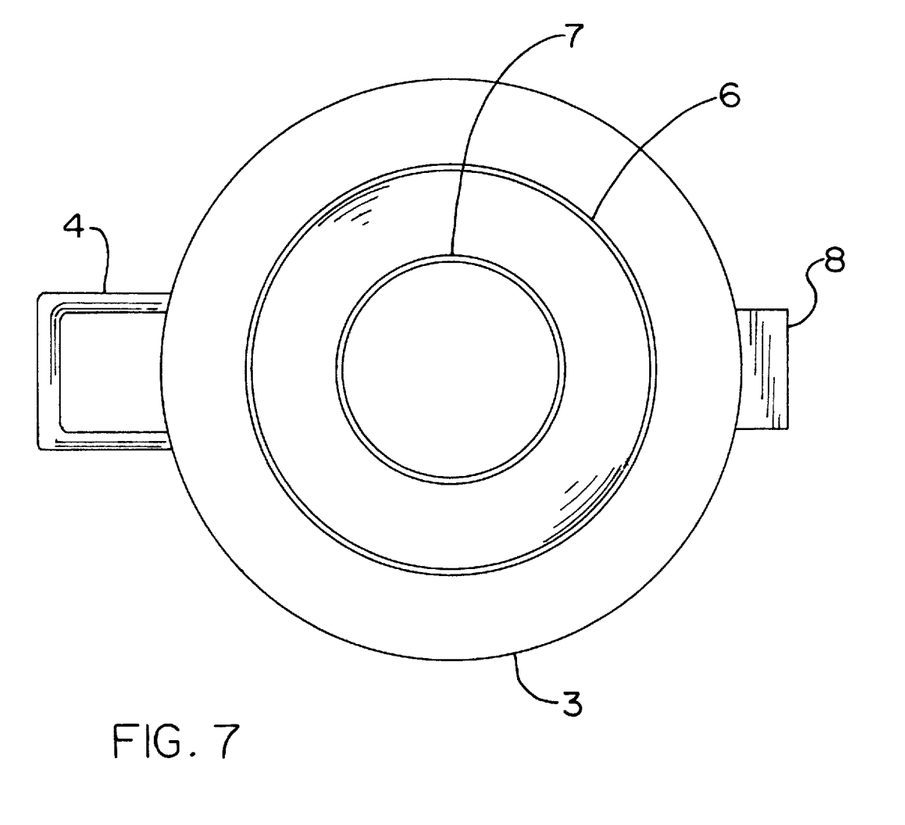
FIG. 7 is an enlarged cross-sectional view of the lid in accordance with the present invention taken along 4—4 of FIG. 1

Referring now to the drawings, and more particularly to FIG. 2, a three piece, bulb-type syringe is shown including a syringe barrel 12, a recloseable lid 3 and a seperate compressible and resilet syringe bulb 1 removeably connected in frictional engagement to the recloseable lid 3 which frictionally connects into the proximal end of syringe barrel 12. Barrel 12 is shown including a cylindrical shaft having a diameter 17 which tapers radially inwardly at the distal end of the barrel and connects with a hollow, integral syringe tip 15 (FIG. 1) which frictionally receives a cap 14. Frictionally connected inside the proximal end of the barrel 12 is the neck portion 7 of lid 3. This neck portion 7 has an aperture which frictionally fits down inside of the barrel 12. The lid 3 also has an aperture 6 that allows the syringe bulb 1 to rest inside of the lid 3 while the neck 7 of the lid 3 frictionally engages the neck 2 of the bulb 1 in an airtight frictional seal. When the syringe is in the closed mode (Fig. 2 ) ready for use, there are two airtight frictional seals which are occuring simultaneously. One seal is created between the neck 7 of the lid 3 and the neck 2 of the syringe bulb 1, which is accomplished by the bulb being made of a rubbery material and the lid being made of a rigid plastic material. The second airtight frictional seal is created between the neck 7 of lid 3 and the interior wall of barrel 12, which is accomplished by the lid 3 being made of a rigid plastic material and the barrel 12 of the syringe likewise being made of the same material. The neck 7 of the lid 3 is slightly smaller in diameter than the diameter 17 of the barrel 12 and the distal end of the neck 7 of the lid 3 is slightly tappered inwardly 16 on the outer circumference and thus when the neck 7 of the lid 3 is manually forced into the barrel 12 of the syringe an airtight frictional seal is made. The lid 3 of this present invention rests on top of the funnel shaped portion 10 of the syringe when in the closed position FIG. 2. The lid 3 has an outer flange 18 that is used to snap onto the upper rim 9 at the top of the funnel shaped portion 10 of the syringe, when in the closed mode. The lid 3 and the syringe bulb 1 resting inside of the lid 3 can be extracted from the barrel 12 of the syringe simultaneously by simply lifting upward on tab 8 which disengages the frictional connection between the neck 7 of the lid 3 and barrel 12, as the lid 3 and bulb 1 are pivotted up and away from the barrel of the syringe. The airtight frictional seal between the syringe bulb 1 and the lid 3 can be broken by manually extracting the bulb from the lid, not when the lid 3 is pivotted up and away from the barrel 12. When the lid 3 and the bulb 1 are extracted the syringe is then employed as a funnel and if necessary the syringe can be quickly fuctionable by the user simply closing the lid onto the funnel headed syringe and thereby creating the frictional airtight seal between the neck 7 of the lid 3 and the barrel 12 of the syringe once again. The pivotting action of the lid 3 is acomplished by the lid 3 possessing a "u" shaped bar 4 on the outer circumference of the lid (illustrated in FIG. 3 and FIG. 7) and the funnel headed portion 10 of the syringe having an extension peice 5 possessing a "c" shaped configuration 11 that is adapted for recieving the "u" shaped bar 4 of the lid 3. When the two are joined by snapping the bar 4 in opening 11 a pivotting hinge is created capable of extracting and engaging the lid 3 and attached bulb 1 to and from the syringe quickly and efficiently. The pivotting action of the present invention is best illustrated in FIG. 5 (A&B) and FIG. 6. There are three integral working parts of the present invention. (1)The syringe bulb 1 rest inside of the lid 3 with the neck 2 of the bulb 1 in frictional engagement with the neck 7 of lid 3 creating an airtight seal. (2)The lid 3 has a neck 7 that fits down inside of barrel 12 in an airtight frictional fit while simultaneously holding the syringe bulb 1 in an airtight frictional fit. The lid 3 and the syringe bulb 1 resting inside may be removed from the barrel 12 of the syringe by means of a snap together hinge created by bar 4 of lid 3 and the "c" shaped receiving structure 11 of funnel extension 5. (3)The funnel headed syringe who's barrel recieves the neck 7 of the lid 3 in an airtight frictional fit.

In closing when the pivotting lid 3 and the syringe bulb 1 are extracted from the barrel 12 of the syringe the user has a large funnel headed syringe with a large working surface area at the top of the syringe in which to channel liquids and pureed food down the barrel 12 of the syringe quicker and more efficiently without wasting the feeding or making a mess. The sloping angles 10 of the funnel headed syringe would eliminate the need for finger tabs on the outside of the barrel of the syringe. When the user desires to compress the bulb they would clasp the sloping angle portion 10 of the funnel headed syringe with their index and middle fingers which acts as finger tabs for the syringe. The user can grasp the funnel headed portion 360 degrees at any point and compress the bulb without futher manipulation of the syringe because there are no finger tabs to line up for grasping. The funnel headed syringe would help prevent the overflow of duodenal contents from overflowing while feeding a tube patient due to reflux. Also by the present invention possessing a 30 bulb-extracting pivotting lid the user would not have to keep up with the syringe bulb after being extracted from the syringe and would greatly reduce the chance of the user's hand contaminating the bulb because the user would not have to touch the bulb during extracton or insertion to and from the syringe, but would manipulate the lid instead. The present invention, a funnel headed bulb-type syringe possesing a pivotting bulb extracting lid would simplify the process of feeding patients requiring the use of such devices.

I claim:

1. A two part irrigational syringe and feeding tube system for feeding patients, said feeding tube system comprising: a first part syringe having a barrel so as to form a passage for food having an inside diameter and having a front end and a back end, a funnel shape projection in connection with said back end, said funnel shaped projection having a first narrow opening and a second opening larger than said narrow opening, an outer peripheral portion in connection with said second opening and of larger diameter than said inside diameter, a reclosable lid in pivotal connection with said outer peripheral portion, said lid having a having a flange having an opening, said flange adapted for frictional connection with said inside diameter of said barrel so as to form a substantially airtight connection between said lid and said barrel; a second part squeeze bulb having a neck, said neck adapted to form a substantially airtight connection between said flange and said squeeze ball so as to provide positive and negative pressure to said passage.

2. The apparatus of claim 1 wherein said outer peripheral portion ha s an extended tab portion so as to provide a convenient place for lifting said funnel shaped projection from said syringe.

\* \* \* \* \*